United States Patent
Thomas

(10) Patent No.: US 9,155,831 B2
(45) Date of Patent: Oct. 13, 2015

(54) APPARATUSES AND METHODS FOR DETECTING GAS CONTAMINATION

(75) Inventor: Ray Gerald Thomas, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 238 days.

(21) Appl. No.: 13/813,009

(22) PCT Filed: Aug. 3, 2011

(86) PCT No.: PCT/US2011/046368
§ 371 (c)(1),
(2), (4) Date: Jan. 29, 2013

(87) PCT Pub. No.: WO2012/018883
PCT Pub. Date: Feb. 9, 2012

(65) Prior Publication Data
US 2013/0131508 A1    May 23, 2013

Related U.S. Application Data

(60) Provisional application No. 61/370,548, filed on Aug. 4, 2010.

(51) Int. Cl.
| | |
|---|---|
| A61M 5/00 | (2006.01) |
| G01N 21/67 | (2006.01) |
| A61B 6/00 | (2006.01) |
| A61M 25/00 | (2006.01) |
| A61M 39/22 | (2006.01) |

(52) U.S. Cl.
CPC ............. *A61M 5/007* (2013.01); *A61B 6/481* (2013.01); *A61M 25/00* (2013.01); *G01N 21/67* (2013.01); *A61M 2039/226* (2013.01); *A61M 2205/18* (2013.01); *A61M 2205/3306* (2013.01); *A61M 2205/3313* (2013.01); *A61M 2205/3592* (2013.01); *A61M 2205/505* (2013.01); *A61M 2205/52* (2013.01); *A61M 2205/702* (2013.01)

(58) Field of Classification Search
CPC ............. A61M 2205/3306; A61M 2205/3313; G01N 21/67; G01J 3/443
USPC .......................................... 356/313; 600/532
See application file for complete search history.

(56) References Cited

U.S. PATENT DOCUMENTS

| | | | | |
|---|---|---|---|---|
| 4,060,708 | A | * | 11/1977 | Walters .......................... 356/313 |
| 4,592,368 | A | | 6/1986 | Ricciardelli et al. |
| 4,766,318 | A | * | 8/1988 | Adler-Golden et al. ....... 356/313 |
| 5,249,579 | A | | 10/1993 | Hobbs et al. |
| 6,215,406 | B1 | * | 4/2001 | Chen ............................. 340/632 |

(Continued)

OTHER PUBLICATIONS

The International Search Report and Written Opinion dated Apr. 6, 2012.

(Continued)

*Primary Examiner* — Kara E Geisel
(74) *Attorney, Agent, or Firm* — Thomas Horstemeyer, LLP

(57) ABSTRACT

In one embodiment, a gas contamination detection apparatus includes a gas analyzer adapted to receive a sample of a gas to be delivered to a patient and to analyze the gas sample to determine whether the gas contains a contaminant, and a gas shut-off valve adapted to automatically prevent the gas from being delivered to the patient if the gas is determined to contain a contaminant.

26 Claims, 3 Drawing Sheets

(56) References Cited

U.S. PATENT DOCUMENTS

| | | | |
|---|---|---|---|
| 6,236,041 B1 * | 5/2001 | Donnerhack et al. | 250/281 |
| 6,427,687 B1 | 8/2002 | Kirk | |
| 6,494,777 B1 | 12/2002 | Chiang | |
| 6,584,974 B1 | 7/2003 | Ratner | |
| 6,645,197 B2 | 11/2003 | Garrison et al. | |
| 7,621,171 B2 | 11/2009 | O'Brien | |
| 7,717,109 B2 | 5/2010 | Fukunaga et al. | |
| 2001/0044618 A1 | 11/2001 | Recinella et al. | |
| 2005/0222491 A1 | 10/2005 | Noda et al. | |

OTHER PUBLICATIONS

Hawkins, et al., Carbon Dioxide (CO2) Digital Subtraction Angiography: 26-year Experience at the University of Florida, European Radiology, Issue vol. 8, No. 3, Mar. 1998.

* cited by examiner

APPARATUSES AND METHODS FOR DETECTING GAS CONTAMINATION

CROSS-REFERENCE TO RELATED APPLICATION

This application is the 35 U.S.C. §371 national stage of PCT application PCT/US2011/46368, filed Aug. 3, 2011, which claims priority to and the benefit of U.S. Provisional Application No. 61/370,548, filed Aug. 4, 2010, both of which are hereby incorporated by reference in their entirety.

BACKGROUND

In recent years, it has become common to use carbon dioxide ($CO_2$) gas as a contrast agent in angiography. $CO_2$ works well as a contrast agent and, unlike iodine which can cause complications for some patients, $CO_2$ is well tolerated by nearly all patients. In addition, $CO_2$ is inexpensive and, because of its high solubility, quickly leaves the body through normal respiration.

$CO_2$ is typically delivered to the body through a gas delivery system that can, for example, comprise a $CO_2$ source such as a bag filled with the gas, a delivery means such as a syringe or pump, and a catheter. Unfortunately, it is possible for leaks to develop in such a system that enable air to enter system and, therefore, the patient. While the oxygen gas within air is relatively harmless, the nitrogen gas within the air can cause serious health problems, including ischemia. Therefore, it is important when performing $CO_2$ angiography to ensure that air does not enter the gas to be delivered to the patient. Although systems and methods have been proposed for detecting such contaminants, none are presently known that are simple, inexpensive, and immediate.

BRIEF DESCRIPTION OF THE DRAWINGS

The disclosed apparatuses and methods can be better understood with reference to the following drawings. The components in the drawings are not necessarily to scale.

DETAILED DESCRIPTION

As described above, it is important to ensure that contaminants, such as air, are not present in contrast agents, such as $CO_2$ gas, that are delivered to a patient during a medical procedure, such as $CO_2$ angiography. Disclosed herein are apparatuses and methods for detecting such contaminants. In some embodiments, the apparatuses and methods are specifically configured to detect nitrogen gas within $CO_2$ gas that is supplied by an angiographic $CO_2$ delivery system. In some embodiments, detection is performed by obtaining a sample of the gas and analyzing it with an optical spectrometer. When a contaminant is detected, delivery of gas to the patient is prevented.

In the following discussion, various embodiments are described. It is to be understood that those embodiments are mere examples of the disclosed inventions and that other embodiments are possible. All such other embodiments are intended to fall within the scope of the present disclosure.

Figure 1:
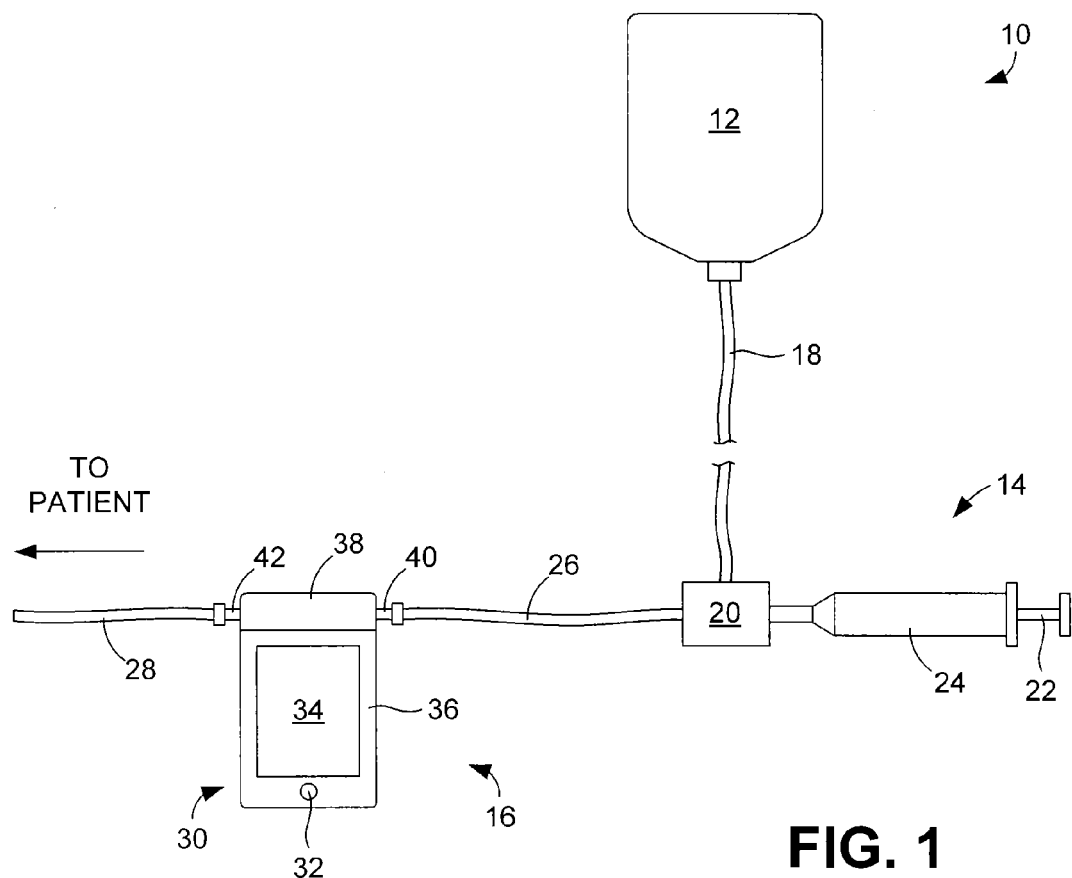
FIG. 1 is diagram of an embodiment of a gas delivery system, such as an angiographic $CO_2$ delivery system, that includes a gas contamination detection apparatus.

FIG. 1 illustrates an example embodiment of a gas delivery system 10. For purposes of this discussion, it is assumed that the system 10 is an angiographic $CO_2$ delivery system. As indicated in FIG. 1, the system 10 generally includes a source 12 of $CO_2$ gas, a gas driving means 14, and a gas contamination detection apparatus 16. By way of example, the source 12 of $CO_2$ gas comprises a bag that is filled with the gas from which gas can be drawn using the gas driving means 14, which can comprise a syringe. The gas can travel from the source 12 to the driving means 14 via a tube 18 that extends to a connector 20 to which the driving means is connected. In some embodiments, the connector 20 can comprise a check valve that ensures that gas can only travel from the source 12 to the driving means 14 along the tube 18 and not vice versa.

Once $CO_2$ gas has been drawn from the source 12 and into the driving means 14, the gas can be delivered to the patient. In cases in which the driving means 14 comprises a syringe, a plunger 22 of the syringe can be pressed into a body 24 of the syringe to propel the $CO_2$ gas along a further tube 26 whose proximal end is connected to the connector 20. In some embodiments, a further check valve within the connector 20 ensures that gas can only travel from the driving means 14 into the tube 26 and not vice versa.

The gas contamination detection apparatus 16 is connected to a distal end of the tube 26 and there for receives the gas that is propelled along the tube by the driving means 14. As is described in greater detail below, the gas contamination detection apparatus 16 comprises a gas analyzer that is adapted to analyze the received gas to confirm that it is not contaminated, for example by air and/or nitrogen. If no contamination is detected, the gas can be delivered through the apparatus 16 to a further tube 28 for delivery to a patient. By way of example, the tube 28 can comprise a catheter that is inserted into a blood vessel of the patient. If contamination is detected, however, the gas contamination detection apparatus 16 can automatically prevent gas delivery to the patient via the tube 28 to prevent the possibility of patient injury.

As is suggested by FIG. 1, the gas contamination detection apparatus 16 can be configured as a stand-alone, handheld gas contamination detection device. In the illustrated example, the apparatus 16 comprises a housing 30 that is sized and configured to be held within a user's hand. In some embodiments, the housing 30 has dimensions similar to a smart phone or a tablet computing device. The housing 30 supports a user interface that enables a user to communicate commands to the apparatus 16. By way of example, the user interface includes at least one button 32 and a touch-sensitive display 34. In some embodiments, the apparatus 16 comprises a base unit 36 and a removable gas handling unit 38 that incorporates an inlet 40 and outlet 42 of the apparatus. In such cases, the gas handling unit 38 can be made as a one-time-use disposable unit that is replaced after it is used to deliver gas to a patient.

Although a handheld device embodiment is illustrated in FIG. 1, it is noted that such a configuration is not necessary. In other embodiments, the various components of the gas contamination detection apparatus can be otherwise integrated into an angiographic $CO_2$ delivery system, including automated gas delivery systems (not shown).

Figure 2:
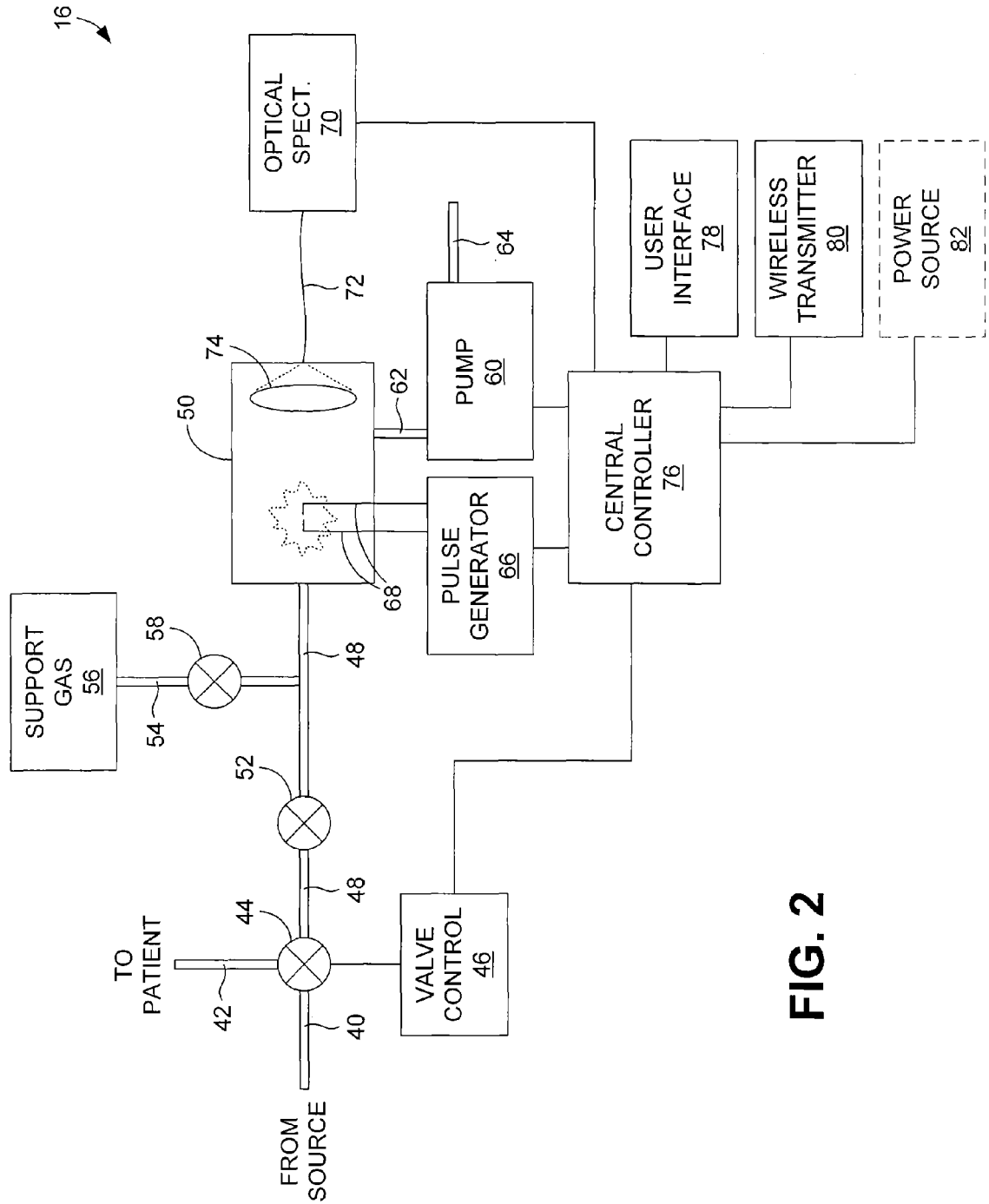
FIG. 2 is a schematic diagram of an embodiment of the gas contamination detection apparatus shown in FIG. 1.

FIG. 2 schematically illustrates an example configuration for the gas contamination detection apparatus 16 shown in FIG. 1. In the embodiment shown in FIG. 2, the apparatus 16 includes gas shut-off valve 44 that is connected to both the inlet 40 and the outlet 42. The gas shut-off valve 44 can be placed into at least two different states, one in which gas can flow from the inlet 40 into the outlet 42, and another in which gas cannot flow from the inlet into the outlet. In some embodiments, the gas shut-off valve 44 is a solenoid valve that is electronically controlled with a valve control 46.

The inlet 40 and/or the gas shut-off valve 44 is in fluid communication with a gas delivery tube 48 that can be used to deliver gas received by the apparatus 16 to a plasma chamber 50 in which the spectrum of a plasma generated from the gas can be analyzed. As is shown in FIG. 2, a flow controller 52 can be provided along the delivery tube 48 to control (e.g., limit) the flow of gas to the plasma chamber 50. In some embodiments, the flow controller 52 comprises a needle valve. In addition to the flow controller 52, a support gas delivery tube 54 can be connected to the delivery tube 48 so that a support gas contained in a container 56 can also be delivered to the plasma chamber 50. As is also described below, the support gas can improve the efficiency of the plasma generation. A further flow controller 58 can be provided along the delivery tube 54 to control (e.g., limit) the flow of support gas to the plasma chamber 50.

With further reference to FIG. 2, a pump 60 is in fluid communication with the plasma chamber 50 and functions to both draw gas (e.g., a mixture of $CO_2$ gas and support gas) into the plasma chamber and lower the pressure of that gas. In cases in which the gas contamination detection apparatus 16 is a handheld device, the pump 60 can comprise a miniature vacuum pump. In some embodiments, the pump 60 comprises a micro diaphragm pump that operates as an oscillating displacement pump. The circular power from a pump motor is converted into vertical movement by an eccentric arm. This motion is then transferred to a diaphragm by means of a connecting rod that, in conjunction with an inlet and outlet valve, creates a vacuum. In some embodiments, the pump 60 can produce vacuum up to approximately 8.85 inches of mercury (in. Hg) and has dimensions of approximately 36.5 millimeters (mm)×22.4 mm×50.5 mm. As is shown in FIG. 2, the pump 60 can be connected to the plasma chamber 50 with a connection tube 62. Gas drawn through the pump 60 can be exhausted to the atmosphere via a vent 64.

As is further shown in FIG. 2, the gas contamination detection apparatus 16 further comprises a pulse generator 66 that is used to generate the plasma within the plasma chamber 50. More particularly, the pulse generator 66 is configured to deliver a high-voltage pulse via electrodes 68 that extend into the plasma chamber 50. The pulse causes an electric arc to form between the electrodes 68 that ionizes the gas and generates a plasma discharge whose optical emission spectrum can be evaluated. In some embodiments, the pulse generator 66 uses an adjustable, high-frequency output power supply. The input voltage is 12 volt DC and the output is adjustable over a range of approximately 1 to 7 kilovolts (kV) AC with an operating frequency of approximately 25 to 32 kilo Hertz (kHz). In some embodiments, the power supply has dimensions of approximately 32 mm×34.7 mm×78 mm. In other embodiments, the power supply can be a small power step-up transformer and a power transistor. In this configuration, high-voltage output is obtained with charging and discharging cycles, controlled by a controller (e.g., controller 76 described below) and the power transistor. Current is enabled to flow in a primary winding of the transformer while charging and discharging into a secondary winding when the power transistor is turned off, thus producing a high-voltage pulse (e.g., an approximately 2 to 4 kV pulse).

The emission spectrum can be detected using an optical spectrometer 70 that also forms part of the apparatus 16. The light spectrum can be delivered to the optical spectrometer 70 via an optical waveguide 72, such as an optical fiber. In some embodiments, the light from the plasma can be focused into the optical waveguide 72 using a lens 74 that also converts divergent beams of light into a parallel beam (i.e., collimates the light). In some embodiments, the optical spectrometer 70 uses a silicon NMOS photodiode detector array for superior ultraviolet (UV) sensitivity and reduced crosstalk. Such spectrometers outperform traditional CCD-based instruments, particularly in the UV spectrum. The spectrometer 70 can comprise an integrated order-sorting filter and have low stray light for low-light signal measurements. The spectrometer is F/# matched to minimize sensitivity loss from the optical mismatch between the fiber optic's numerical aperture and the array's aperture. Example parameters for the optical spectrometer 70 include:

Wavelength range: 190-800 nm
Wavelength accuracy: +/−0.5 nm
Wavelength reproducibility: +/−0.1 nm
Stray light: 0.7% @ 210 nm
Dynamic range: 300:1 (single scan)
Integration time: 17 ms-1 minute
Entrance slit: 25 um×1 mm
Detector: 1024 element silicon NMOS photodiode array
Focal length: 150 mm
F/#: 2.6
A/D converter: 16-bit
Power: 12 V DC, 0.2 A
PC interface: USB 2.0
Operating temperature: 0-50° C.

Operation of the valve control 46, pump 60, and pulse generator 66 can be controlled by a central controller 76. The central controller 76 can, for example, comprise a microprocessor that includes instructions (i.e., logic) that controls the operation of the gas contamination detection apparatus 16. In addition, the central controller 76 is further configured to analyze the emission spectrum detected by the optical spectrometer 70. In particular, the controller 76 is configured to identify the peaks in the spectrum data that correspond to a contaminant, such as nitrogen or oxygen.

Also shown in FIG. 2 are a user interface 78, a wireless transmitter 80, and an internal power source 82. The user interface 78 is used to control operation of the gas contamination detection apparatus 16. An example embodiment for the user interface 78 has been described above in relation to FIG. 1. When provided, the wireless transmitter 80 can be used to transmit data to another apparatus. By way of example, a detected emission spectrum or the results of evaluation of the spectrum can be wirelessly transmitted to a computing device for analysis and/or record keeping. The power source 82 can comprise a battery that supplies power to each power-using component of the apparatus 16, such as the valve control 46, pump 60, pulse generator 66, optical spectrometer 70, central controller 76, user interface 78, and wireless transmitter 80. Although an internal power source 82 is shown in FIG. 2, it is noted that an external power source, such as a wall power outlet, can be used to supply power to the components of the apparatus 16, if desired.

An example embodiment of an angiographic gas delivery system 10 and a gas contamination detection apparatus 16 having been described above, operation of the system and apparatus will now be described. For the purposes of this example, it will be assumed that the gas to be delivered to the patient is $CO_2$ gas and the contaminant to be monitored for is nitrogen. It is noted, however, that the system 10 and apparatus 16 could be used to respectively deliver and detect other gases, if desired.

When $CO_2$ gas is to be delivered to a patient, the catheter 28 (after having been purged of air) is inserted within the blood vessel that is to be imaged. The $CO_2$ gas can be delivered through the inlet 40 and the gas shut-off valve 44, and into the gas delivery tube 48. Such delivery can be effected by operation of the driving means 14 and/or operation of the pump 60. Notably, the gas does not flow through to the outlet 42 (which leads to the patient) because, in the initial state, the shut-off valve 44 is closed. The flow controller 52 provided along the delivery tube 48 restricts the volume of gas that can flow into the plasma chamber 50. By way of example, the flow controller 52 restricts the flow of gas to approximately 5 to 50 milliliters per minute (ml/min). When a support gas is also to be delivered to the plasma chamber 50, the support gas can flow through the delivery tube 54 and the flow controller 58 and into the delivery tube 48 for delivery into the chamber. The support gas is selected to have a higher excitation potential than nitrogen and therefore can transfer its excitation energy to the nitrogen. By way of example, the support gas can comprise helium and/or argon gas. The presence of a support gas results in a higher efficiency energy transfer process and enables the use of less power, smaller volumes of gas, and higher pressures within the plasma chamber 50.

As noted above, the pump 60 can be used to draw both the $CO_2$ gas and the support gas into the plasma chamber 50. By way of example, the pump 60 draws the gas into the plasma chamber at a rate of approximately 10 to 75 ml/min. Operation of the pump 60 also serves to lower the pressure within the plasma chamber 50 to assist in the generation of the plasma. By way of example, the pump 60 reduces the pressure within the plasma chamber 50 to a range of approximately 5 to 10 in. Hg.

Once a gas sample has been drawn into the plasma chamber 50, a high-voltage pulse is delivered by electrodes 68 to ionize the gas and generate a plasma discharge whose optical emission spectrum can be detected by the optical spectrometer 70. In some embodiments, the optical spectrometer 70 uses a diffraction grating that redirects light at wavelength-dependent angles and focuses the spectra onto a detector array, such as a charge-coupled detector (CCD) array. This technique differs from Raman spectroscopy at least in that the Raman affect occurs when light interacts with gas molecules to produce scattered light at a wavelength shifted from the incident light.

The emission spectrum detected by the optical spectrometer 70 is then analyzed by the central controller 76. In particular, the central controller 76 analyzes the peaks of the spectrum data to identify the various components contained with the gas sample. When the gas contamination detection apparatus 16 is used to detect nitrogen gas, the spectrum is analyzed to identify the peaks in the spectrum that correspond to nitrogen. The central controller 76 can statistically process the spectrum data to determine the probability of a contamination event. If the purity of the $CO_2$ gas sample is confirmed, the central controller 76 sends a signal to the valve control 46 to open the shut-off valve 44 so that the $CO_2$ gas can be delivered via the outlet 42 to the patient. At that time, the central controller 76 can signal the user that the $CO_2$ may be delivered to the patient, for example using the driving means 14.

If, on the other hand, the central controller 76 determines that the $CO_2$ gas sample contains a contaminant, such as nitrogen, the shut-off valve 44 is not opened and the central controller 76 can activate an alarm signal. The alarm signal can be communicated by the apparatus 16 (e.g., visually and/or audibly) and/or can be transmitted to another device using the wireless transmitter 80. In addition, the contamination event can be logged on the apparatus 16 or on another device for record keeping purposes.

As mentioned above, if the purity of the $CO_2$ gas is confirmed, the shut-off valve 44 is opened so that the gas can be delivered to the patient. In some embodiments, the purity of the gas can be continually tested during delivery of the gas to the patient to ensure that no air leaks occur. If a leak occurs, the central controller 76 will immediately close the shut-off valve 44 to halt delivery of gas to the patient.

Figure 3:
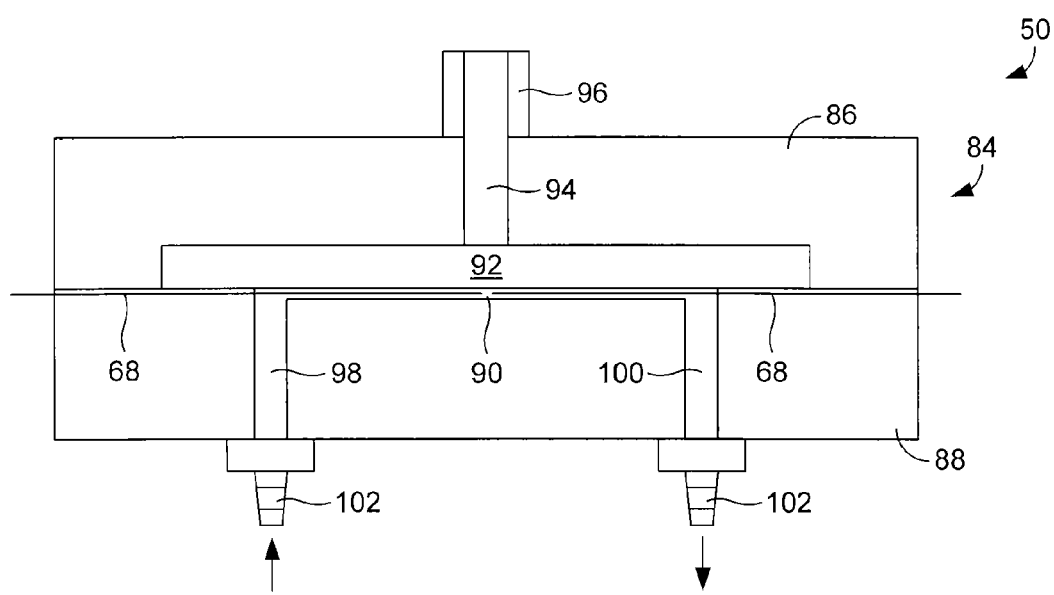
FIG. 3 is a diagram of an embodiment of a plasma chamber that can be used in the gas contamination detection apparatus shown in FIGS. 1 and 2.

FIG. 3 shows an embodiment of the plasma chamber 50 that is particularly well suited for a handheld gas contamination detection device. The plasma chamber 50 generally includes a housing 84. In some embodiments, the housing 84 comprises first and second halves 86 and 88 that together define an interior chamber 90. Defining one wall of the inner chamber 90 is a quartz window 92 that is, for example, positioned within a recess of the first half 86 of the housing 84. An opening 94 extends through the first half 86 to the quartz window 92. The opening 94 is adapted to receive the optical waveguide 72 described above in relation to FIG. 2 so that its end is placed adjacent or in contact with the quartz window 92. A fiber optic connector 96 can be provided on the outside of the first half 86 to facilitate connection of the optical waveguide 72 to the plasma chamber 50. In such an embodiment, a lens (such as the lens 74 shown in FIG. 2) may not be necessary.

Formed through the second half 88 of the plasma chamber 50 are an inlet 98 and an outlet 100 that respectively deliver gas to and remove gas from the inner chamber 90. Barbed connectors 102 can be provided in association with the inlet 98 and outlet 100 to facilitate connection of delivery tubes to the plasma chamber 50.

In some embodiments, the inner chamber 90 comprises a narrow, elongated channel through which gas flows. By way of example, the inner chamber 90 is channel having an approximately 0.5 to 1 mm rectangular (e.g., square) cross-section and is approximately 10 to 12.5 mm long, and has a volume of approximately 2.5 to 12.5 microliters (μl). As is shown in FIG. 3, the electrodes 68 are positioned within the inner chamber 90. By way of example, the electrodes 68 comprise 0.25 mm diameter 99.98% tungsten wires.

Figure 4A:
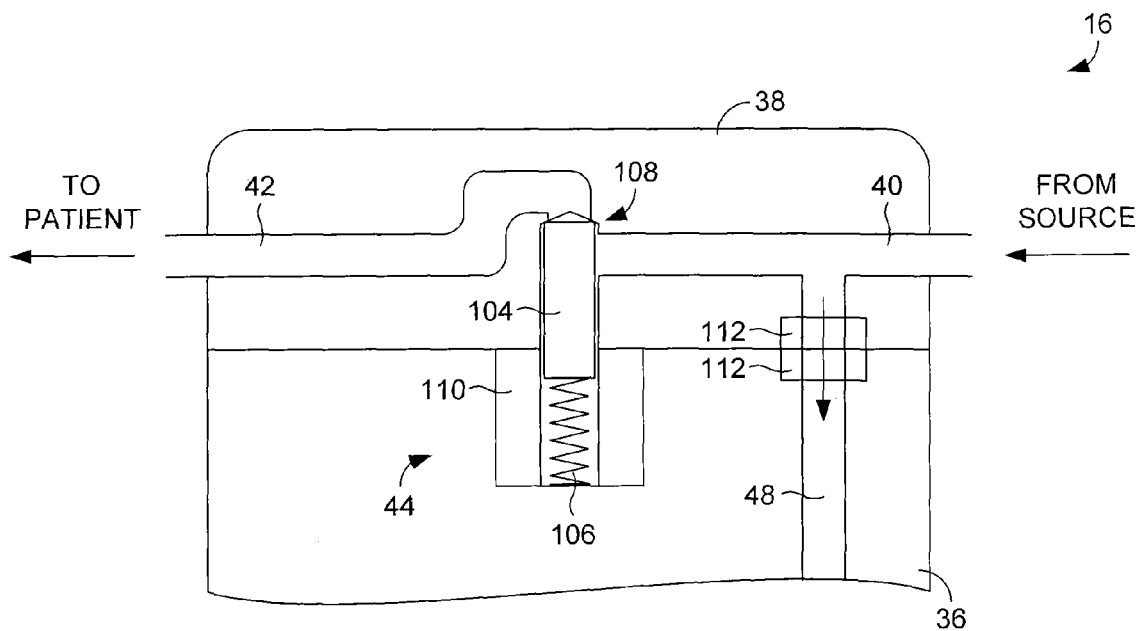
FIGS. 4A and 4B are diagrams that illustrate an embodiment of a handheld gas contamination detection device and operation of the device in preventing and enabling the flow of gas to a patient, respectively.
Figure 4B:
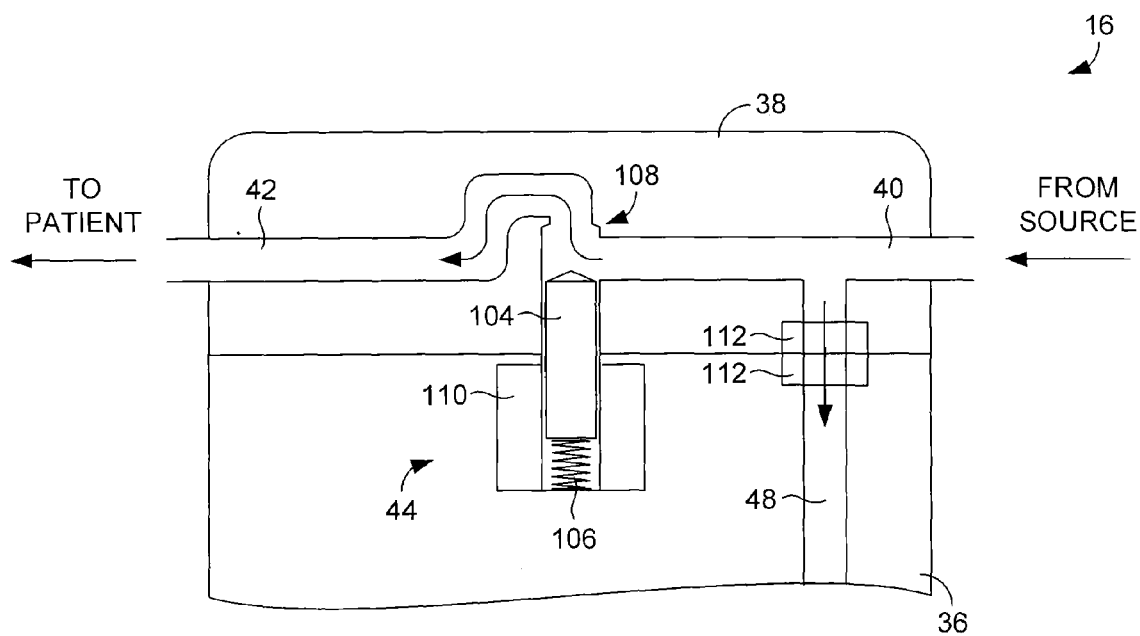

FIGS. 4A and 4B illustrate a handheld embodiment for the gas contamination detection apparatus 16. As indicated above, the apparatus 16 can comprise a base unit 36 and a removable gas handling unit 38 that incorporates the inlet 40 and outlet 42 of the apparatus. FIGS. 4A and 4B also illustrate an embodiment for the gas shut-off valve 44. In the illustrated embodiment, the valve 44 comprises a solenoid valve that includes a plunger 104 that is urged toward a closed position shown in FIG. 4A by a spring 106. In the closed position, the plunger 104 is seated in a valve seat 108.

With further reference to FIGS. 4A and 4B, a coil 110 surrounds the plunger 104. As long as no current runs through the coil 110, the plunger 104 remains in the closed position shown in FIG. 4A and gas cannot flow from the inlet 40 into the outlet 42 (and to the patient). Therefore, the shut-off valve 44 is a normally-closed valve. When an appropriate current is passed through the coil 110, however, an electromagnetic field is generated that pulls the plunger 104 away from the valve seat 108, as shown in FIG. 4B, so that gas can flow from the inlet 40 into the outlet 42. Notably, if power to the apparatus 16 is lost for some reason, power is cut to the shut-off valve 44 and it will automatically close so as to prevent gas from being delivered to the patient. As is also shown in the figures, gas can flow from the inlet 40 and into the delivery tube 48 (which leads to the plasma chamber 50) irrespective of whether the plunger 104 is seated within its valve seat 108 or not. Therefore, gas can be analyzed by the apparatus 16 regardless of whether gas is being delivered to the patient or not.

As described above, the gas handling unit 38 can be can be made as a one-time-use disposable unit that is replaced after it is used to deliver gas to a patient. In such a case, one or more components of the shut-off valve 44, for instance those components that make contact with the gas, can comprise part of the gas handling unit 38 and can therefore be discarded with the unit. For example, the plunger 104 and the spring 106 can be discarded, while the coil 110 is preserved within the base unit 36. In other embodiments, the entirety of the shut-off valve 44 can comprise part of the base unit 36 and can therefore fit within the gas handling unit 38 after it is connected to the base unit. Coupling between the inlet 40 of the gas handling unit 38 and the delivery tube 48 of the base unit 36 can be effected with mating connectors 112.

Claimed are:

1. A gas contamination detection apparatus comprising:
   a gas analyzer configured to receive a sample of a gas to be delivered to a patient and to analyze the sample of the gas to determine whether the gas contains a contaminant, the gas analyzer comprising:
   a chamber configured to receive the sample of the gas;
   a pulse generator configured to generate an electric arc within the chamber that ionizes the sample of the gas to generate a plasma discharge;
   an optical spectrometer that detects an emission spectrum of the plasma discharge;
   a central controller that analyzes the detected emission spectrum and determines whether the gas contains the contaminant; and
   a gas shut-off valve configured to automatically prevent the gas from being delivered to the patient if the sample of the gas is determined to contain the contaminant; and
   wherein the central controller is configured to automatically open the gas shut-off valve if the gas is confirmed to be free of contaminants.

2. The apparatus of claim 1, further comprising a pump configured to draw the sample of the gas into the chamber.

3. The apparatus of claim 1, further comprising a battery that provides power to the pulse generator and the optical spectrometer.

4. The apparatus of claim 1, further comprising a source of support gas that increases an efficiency of plasma generation within the chamber.

5. The apparatus of claim 1, further comprising a display configured to render a user interface, the user interface being configured to obtain user input to be delivered to the apparatus.

6. The apparatus of claim 1, further comprising a wireless transmitter configured to transmit data from the apparatus to a separate device.

7. A gas contamination detection apparatus comprising:
   a chamber adapted to receive a sample of a gas to be delivered to a blood vessel of a patient;
   a pump adapted to draw the sample of the gas into the chamber;
   a pulse generator adapted to generate an electric arc within the chamber that ionizes the sample of the gas to generate a plasma discharge;
   an optical spectrometer adapted to detect an emission spectrum of the plasma discharge;
   a central controller configured to analyze the detected emission spectrum and determine whether the gas is contaminated;
   a gas shut-off valve adapted to automatically prevent the gas from being delivered to the patient; and
   wherein the central controller is configured to automatically open the gas shut-off valve if the gas is confirmed to be free of contaminants.

8. The gas contamination detection apparatus of claim 7, wherein the apparatus is contained within a handheld device.

9. A gas delivery system comprising:
   a catheter configured to deliver a gas from a source of gas into a blood vessel of a patient; and
   a gas contamination detection apparatus provided between the source of gas and the catheter, the gas contamination detection apparatus comprising:
   a gas analyzer configured to receive a sample of the gas to be delivered to the patient and to analyze the sample of the gas to determine whether the gas contains a contaminant; and
   a gas shut-off valve configured to automatically prevent the gas from being delivered from the source of gas to the catheter if the gas is determined to contain the contaminant.

10. The gas delivery system of claim 9, wherein the gas analyzer comprises:
    a chamber adapted to receive the sample of the gas;
    a pulse generator adapted to generate an electric arc within the chamber that ionizes the sample of the gas to generate a plasma discharge; and
    an optical spectrometer that detects an emission spectrum of the plasma discharge.

11. The gas delivery system of claim 10, wherein the gas analyzer further comprises a central controller that analyzes the detected emission spectrum and determines whether the gas is contaminated.

12. The gas delivery system of claim 11, wherein the central controller is configured to automatically open the gas shut-off valve if the gas is confirmed to be free of contaminants.

13. The gas delivery system of claim 10, wherein the gas contamination detection apparatus further comprises a wireless transmitter configured to transmit data from the apparatus to a separate device.

14. The gas delivery system of claim 10, wherein the gas contamination detection apparatus further comprises a battery that provides power to the pulse generator and the optical spectrometer.

15. The gas delivery system of claim 10, wherein the gas contamination detection apparatus further comprises a source of support gas that increases an efficiency of plasma generation within the chamber.

16. The gas delivery system of claim 9, wherein the gas contamination detection apparatus is comprised in a standalone, handheld device.

17. A method for detecting contamination of a gas that is to be delivered to a patient, the method comprising:
    obtaining a sample of the gas;
    analyzing the sample of the gas to determine whether the gas contains a contaminant; and
    automatically preventing the gas from being delivered to the patient if it is determined that the sample of the gas contains the contaminant.

18. The method of claim 17, wherein obtaining the sample of the gas further comprises obtaining a sample of carbon dioxide gas.

19. The method of claim 18, wherein analyzing the sample of the gas further comprises determining whether the sample of the gas contains nitrogen.

20. The method of claim 17, wherein analyzing the sample of the gas further comprises:
   generating a plasma discharge with the sample of the gas;
   detecting an emission spectrum of the plasma discharge; and
   analyzing the emission spectrum to determine whether the sample of the gas contains the contaminant.

21. The method of claim 17, wherein automatically preventing the gas from being delivered further comprises configuring a valve to remain closed through which the gas must pass to reach the patient.

22. The method of claim 17, further comprising mixing the gas with a support gas such that the sample of the gas comprises a mixture of the gas and the support gas to be delivered to the patient.

23. The method of claim 22, wherein the support gas comprises helium gas, argon gas, or a combination thereof.

24. The gas contamination detection apparatus of claim 5, wherein the display further comprises a touch-screen display.

25. The gas contamination detection apparatus of claim 1, further comprising a flow controller provided between a source of gas and the chamber configured to control a flow of the gas to the chamber.

26. The gas contamination detection apparatus of claim 25, wherein the flow controller further comprises a needle valve.

* * * * *